US011464500B2

(12) United States Patent
Jones et al.

(10) Patent No.: US 11,464,500 B2
(45) Date of Patent: Oct. 11, 2022

(54) COMBINED TROCAR AND CANNULA BONE MARROW ASPIRATION DEVICE WITH INTEGRAL VALVE AND PORTS FOR ASPIRATION, AND METHODS FOR USING SAME

(71) Applicant: SpineSmith Holdings, LLC, Austin, TX (US)

(72) Inventors: Robert James Jones, Cedar Park, TX (US); Kevin John Patrick Dunworth, Austin, TX (US); John B. Rossman, Austin, TX (US); Richard J. Kana, Lexington, TX (US)

(73) Assignee: SpineSmith Holdings, LLC, Austin, TX (US)

( * ) Notice: Subject to any disclaimer, the term of this patent is extended or adjusted under 35 U.S.C. 154(b) by 563 days.

(21) Appl. No.: 16/173,958

(22) Filed: Oct. 29, 2018

(65) Prior Publication Data

US 2019/0069885 A1 Mar. 7, 2019

Related U.S. Application Data

(63) Continuation-in-part of application No. 14/642,295, filed on Mar. 9, 2015, now Pat. No. 10,137,227.

(60) Provisional application No. 62/578,177, filed on Oct. 27, 2017, provisional application No. 61/950,140, filed on Mar. 9, 2014.

(51) Int. Cl.
*A61B 10/02* (2006.01)
*A61B 17/34* (2006.01)
*A61B 17/16* (2006.01)

(52) U.S. Cl.
CPC ........ *A61B 10/025* (2013.01); *A61B 17/3472* (2013.01); *A61B 17/1637* (2013.01); *A61B 2010/0258* (2013.01); *A61B 2217/005* (2013.01); *A61M 2202/10* (2013.01)

(58) Field of Classification Search
CPC .......... A61B 10/025; A61B 2010/0258; A61B 10/0283; A61M 2039/229
See application file for complete search history.

(56) References Cited

U.S. PATENT DOCUMENTS 4,729,401 A * 3/1988 Raines .................. F16K 15/148
604/246
4,791,937 A * 12/1988 Wang ................. A61B 10/0283
600/565

(Continued)

*Primary Examiner* — Catharine L Anderson
*Assistant Examiner* — Arjuna P Chatrathi
(74) *Attorney, Agent, or Firm* — Winstead PC (57) ABSTRACT

A device comprising a trocar having a first end and comprising a cannulation and at least one fenestration proximal the first end; and a housing comprising a first port configured for the attachment of a first syringe and a second port configured for the attachment of a collection vessel, a first valve configured to selectively permit fluid flow through the cannulation of the trocar to the first port, and a second valve configured to selectively permit fluid flow through the cannulation of the trocar to the second port. The device allows the first syringe to draw up bone marrow in small volumes with high vacuum and then transfer the small draws into the collection vessel. The device may increase the recovery of desired cells residing in the bone marrow to be recovered during a bone marrow aspiration procedure.

17 Claims, 7 Drawing Sheets

(56) References Cited

U.S. PATENT DOCUMENTS

| | | | | |
|---|---|---|---|---|
| 4,969,870 A * | 11/1990 | Kramer | A61B 17/3472 | 604/93.01 |
| 4,989,614 A * | 2/1991 | Dejter, Jr. | A61B 10/0283 | 600/565 |
| 5,275,609 A * | 1/1994 | Pingleton | A61B 17/32002 | 606/167 |
| 5,649,547 A * | 7/1997 | Ritchart | A61B 10/0266 | 600/566 |
| 5,913,859 A * | 6/1999 | Shapira | A61B 17/1635 | 606/180 |
| 6,017,316 A * | 1/2000 | Ritchart | A61B 10/0283 | 600/565 |
| 2002/0038105 A1* | 3/2002 | Schwartz | A61M 39/24 | 604/247 |
| 2002/0045841 A1* | 4/2002 | Stephens | A61B 10/0283 | 600/566 |
| 2002/0058945 A1* | 5/2002 | Steiner | A61B 17/1635 | 606/80 |
| 2002/0082519 A1* | 6/2002 | Miller | A61B 10/025 | 600/566 |
| 2003/0004528 A1* | 1/2003 | Ishikawa | A61B 17/3417 | 606/169 |
| 2003/0208181 A1* | 11/2003 | Geise | A61M 1/0218 | 604/406 |
| 2004/0267154 A1* | 12/2004 | Sutton | A61B 10/025 | 600/562 |
| 2006/0041245 A1* | 2/2006 | Ferry | A61B 90/50 | 604/95.01 |
| 2007/0055284 A1* | 3/2007 | Osorio | A61B 17/1604 | 606/94 |
| 2008/0234715 A1* | 9/2008 | Pesce | A61B 17/32002 | 606/171 |
| 2008/0243028 A1* | 10/2008 | Howard | A61M 1/79 | 600/565 |
| 2013/0131546 A1* | 5/2013 | Azimpoor | A61B 10/0096 | 600/566 |
| 2014/0031772 A1* | 1/2014 | Hardy | A61B 5/150503 | 604/319 |

\* cited by examiner

COMBINED TROCAR AND CANNULA BONE MARROW ASPIRATION DEVICE WITH INTEGRAL VALVE AND PORTS FOR ASPIRATION, AND METHODS FOR USING SAME

BACKGROUND OF THE INVENTION

Field of the Invention

Generally, the present disclosure relates to a medical device for recovering bone marrow from bone.

SUMMARY OF THE INVENTION

The following presents a simplified summary of the disclosure in order to provide a basic understanding of some aspects of the disclosure. This summary is not an exhaustive overview of the disclosure. It is not intended to identify key or critical elements of the disclosure or to delineate the scope of the disclosure. Its sole purpose is to present some concepts in a simplified form as a prelude to the more detailed description that is discussed later.

Generally, the present disclosure is directed to a medical device, comprising a trocar having a first end and comprising a cannulation and at least one fenestration proximal the first end; and a housing comprising a first port configured for the attachment of a first syringe and a second port configured for the attachment of a collection vessel, a first valve configured to selectively permit fluid flow from the at least one fenestration of the trocar through the cannulation of the trocar to the first port, and a second valve configured to selectively permit fluid flow from the first port to the second port.

The present disclosure also includes a method, comprising: inserting a first end of a trocar into a bone, wherein the trocar is a component of a medical device comprising the trocar, wherein the trocar comprises a cannulation and at least one fenestration proximal the first end, and a housing comprising a first port configured for the attachment of a first syringe and a second port configured for the attachment of a collection vessel, a first valve configured to selectively permit fluid flow from the at least one fenestration of the trocar through the cannulation of the trocar to the first port, and a second valve configured to selectively permit fluid flow from the first port to the second port; attaching a first syringe to the first port and a collection vessel to the second port; drawing up bone marrow from the bone by the first syringe; and collecting the bone marrow in the collection vessel.

The present disclosure also relates to a medical device system, comprising a medical device, comprising a trocar having a first end and comprising a cannulation and at least one fenestration proximal the first end; and a housing comprising a first port configured for the attachment of a first syringe and a second port configured for the attachment of a collection vessel, a first valve configured to selectively permit fluid flow from the at least one fenestration of the trocar through the cannulation of the trocar to the first port, and a second valve configured to selectively permit fluid flow from the first port to the second port, and a servo motor configured to open and close the first valve and the second valve; and a robotic subsystem comprising at least one servo motor controller configured to control the servo motor and a controller configured to control the operation of the robotic subsystem.

The present disclosure may provide improved recovery of bone marrow from bone.

The present application hereby incorporates by reference herein U.S. Provisional Patent Application 62/578,177, filed Oct. 27, 2017.

BRIEF DESCRIPTION OF THE DRAWINGS

The disclosure may be understood by reference to the following description taken in conjunction with the accompanying drawings, in which like reference numerals identify like elements, and in which.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION

Various illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Embodiments herein are directed to devices for recovering bone marrow from bone, as well as methods of using such devices. For example, embodiments herein are directed to a medical or surgical instrument having a trocar device or a trocar/cannula combined device.

Generally, a combined trocar/cannula with integral valve and dual ports is designed to improve the recovery of desired cells residing in the bone marrow to be recovered during a bone marrow aspiration procedure. This combined trocar allows two syringes to be attached in order for a small syringe to draw up bone marrow in small volumes with high vacuum and then transfer the small draws into the larger collection syringe that is also attached to the combined trocar/cannula.

In one embodiment, each port of the combined trocar/cannula has a port-specific valve.

In one embodiment, the combined trocar/cannula has a first end configured for penetrating bone. For example, the first end may be rigid and pointed. In another embodiment, for example, the first end may be rigid, pointed, and threaded.

This combined trocar/cannula may be used with a drilling device, a hammer, a handle, or other instruments capable of aiding in such intrusion in order to aid in penetrating the bone to access the bone marrow for aspiration.

In addition to a device as described above, the present disclosure also relates to a method, comprising: inserting a first end of a trocar into a bone, wherein the trocar comprises a first port configured for the attachment of a first syringe and a second port configured for the attachment of a collection vessel; attaching a first syringe to the first port and a collection vessel to the second port; drawing up bone marrow from the bone by the first syringe; and collecting the bone marrow in the collection vessel.

Methods according to the present disclosure may allow the improved recovery of bone marrow from bone. "Improved recovery" encompasses one or more of collection of larger volumes of bone marrow or an increase in the amount of desired cells recovered.

Particular embodiments of the present disclosure will now be described in detail with reference to FIGS. 1-8.

Figure 1:
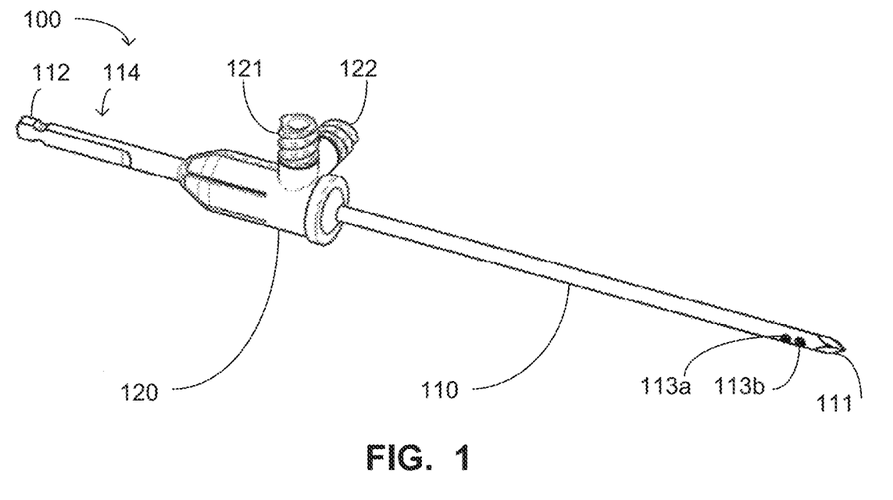
FIG. 1 provides a perspective view of a medical device comprising a trocar and a housing, in accordance with embodiments herein.

FIG. 1 provides a perspective view of a medical device 100, in accordance with embodiments herein. The medical device 100 comprises a trocar 110 and a housing 120. The trocar 110 has a first end 111 and a second end 112. In one embodiment, as shown in FIG. 1, the first end 111 may be rigid and pointed. In another embodiment, not shown, the first end 111 may be rigid, pointed, and threaded.

The trocar 110 also comprises, proximal to the first end 111, at least one fenestration 113. For example, in the depicted embodiment, the trocar 110 comprises two fenestrations 113a and 113b. The at least one fenestration (113a and/or 113b, collectively "113") is in fluid communication with a cannulation (not visible in FIG. 1 but described below with reference to FIGS. 4-6) inside the trocar 110 and running from a position between the first end 111 and the fenestration 113 closest to the first end 111 to a position between first and second ports 121 and 122 (described in more detail below) and the second end 112 of the trocar 110.

Proximal to the second end 112 of the trocar 110 is a handle 114. The handle 114 may be configured for manual manipulation by a human operator of the medical device 100, automated manipulation by a robotic subsystem (described in more detail with reference to FIG. 7, below), or both.

The trocar 110 may be formed from any material suitable for applications in a human body. For example, the trocar 110 may comprise stainless steel.

The medical device 100 also comprises a housing 120. The housing 120 comprises a first port 121 and a second port 122. Each of the first port 121 and the second port 122 are configured for the attachment of syringes. For example, and as depicted in FIG. 1, the first port 121 and the second port 122 may each comprise a luer fitting, to which an appropriately configured syringe or collection vessel (e.g., a second syringe, a connector on a tubing connecting to a vessel, etc.) may be threadably attached in a convenient and reversible manner. The first port 121 and the second port 122 are in fluid communication with the at least one fenestration 113 through the cannulation of the trocar 110, as will be described in more detail later.

The housing 120 may be formed from any material suitable for medical applications, including contact with human bodily fluids, including bone marrow. For example, the housing 120 may be formed from a medically appropriate plastic, medically appropriate metal (e.g., titanium, titanium alloy, zirconia, gold-copper alloy, gold-chromium alloy, stainless steel, niobum, tantalum, etc.), medically appropriate ceramic (e.g., aluminium oxide, zirconium, oxide material, etc.), medically appropriate polymer (e.g., Polyethylene, Polyamide Polymethylmethacrylate, Polytetrafluroethylene, Polyurethane, etc.), and/or the like.

Figure 2:
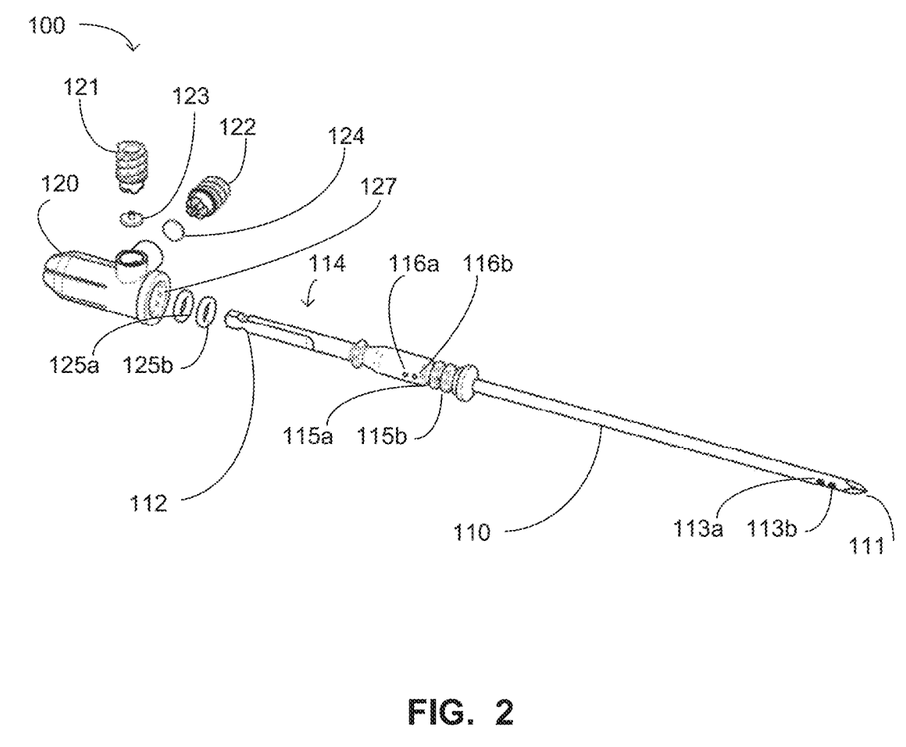
FIG. 2 provides an exploded perspective view of the medical device of FIG. 1, in accordance with embodiments herein.

Turning to FIG. 2, an exploded perspective view of the medical device of FIG. 1 is provided, in accordance with embodiments herein. FIG. 2 provides more detail regarding how the trocar 110 and the housing 120 are connected, and shows first and second valves 123 and 124 disposed between the cannulation of the trocar 110 and the first and second ports 121 and 122, respectively.

The housing 120 has an annular main body that permits the insertion of the second end 112 of the trocar 110 into a longitudinal cavity 127 of the housing 120. At least one rotation-permitting seal 125, such as, in the depicted embodiment, two rotation-permitting O-rings 125a and 125b, are introduced over the second end 112 of the trocar 110 and seated in matching grooves 115, such as, in the depicted embodiment, grooves 115a and 115b, respectively. The at least one rotation-permitting seal 125 arrests insertion of the trocar 110 into the housing 120 at a desired longitudinal position of the trocar 110 relative to the housing 120. The at least one rotation-permitting seal 125 also maintains the longitudinal position of the trocar 110 relative to the housing 120 while permitting rotation of the trocar 110 relative to the housing 120. In other embodiments, not shown, the longitudinal position of the trocar 110 may be fixed relative to the housing 120 in a manner that prevents rotation of the trocar 110 relative to the housing 120.

Turning to the valves 123 and 124, as shown in FIG. 2, the first valve 123 is configured to selectively permit fluid flow from the at least one fenestration 113 of the trocar 110 through the cannulation of the trocar 110 to the first port 121, and a second valve 124 configured to selectively permit fluid flow from the first port 121 to the second port 122. In the embodiment depicted in FIG. 2, the first valve 123 and the second valve 124 are diaphragms configured to be deformable upon the application of positive or negative pressure. For example, the first valve 123 and the second valve 124 may comprise silicone with a sufficient combination of thinness and pliability to permit deformation upon the application of positive or negative pressures of a magnitude achievable by a human operator or a robotic subsystem depressing or withdrawing the plunger of a syringe.

FIG. 2 also shows that the trocar 110 comprises at least one exit fenestration 116. For example, FIG. 2 shows two exit fenestrations 116a and 116b. The cannulation of the trocar 110 extends at least to a position beyond the exit fenestration 116 furthest from the first end 111. The exit fenestration(s) (116a, 116b, collectively "116") are positioned to permit fluid communication from the cannulation of the trocar 110 to the first and second ports 121 and 122, as controlled by the first valve 123 and the second valve 124.

Figure 3:
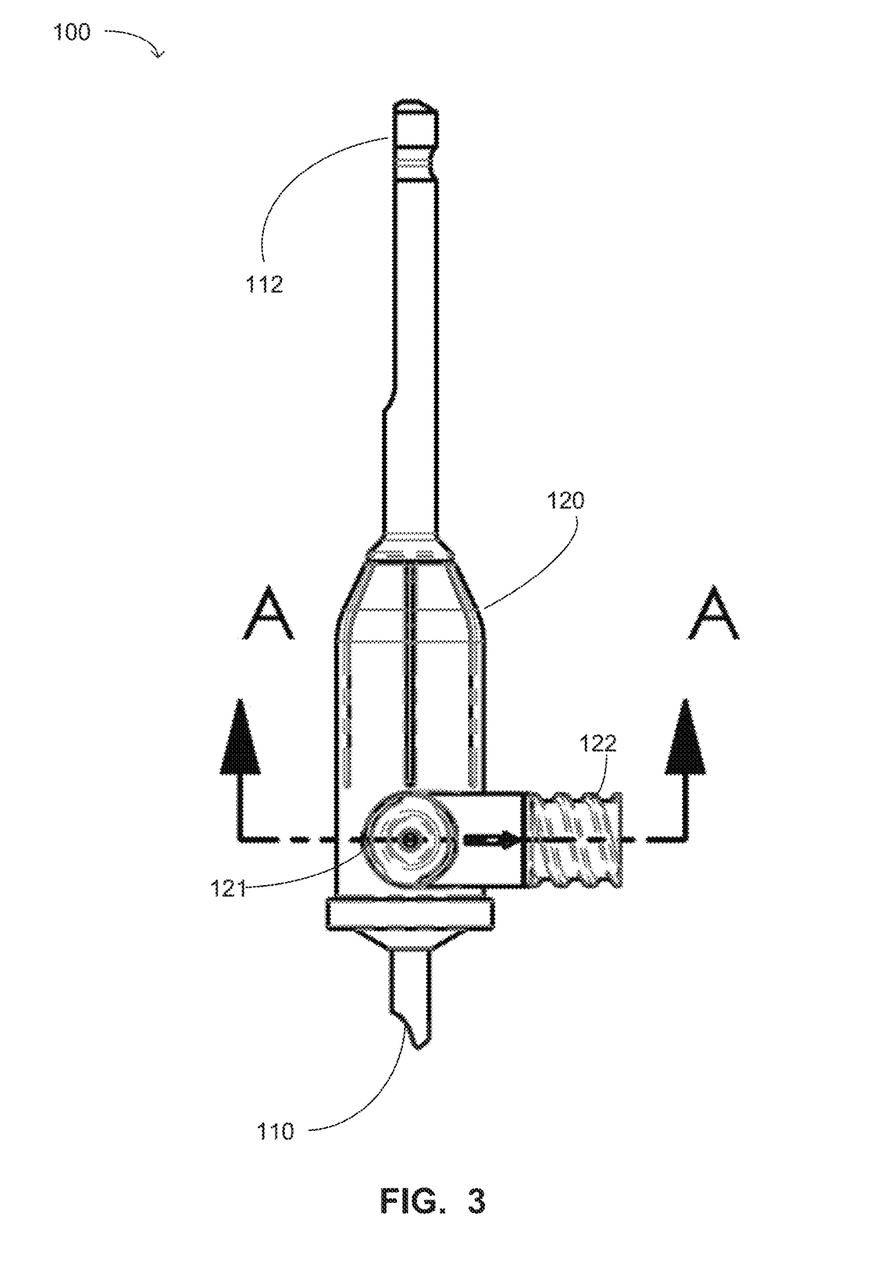
FIG. 3 provides a side view of a portion of the medical device of FIG. 1, in accordance with embodiments herein.

FIG. 3 provides a side view of a portion of the medical device 100, in accordance with embodiments herein. The depicted portion contains the second end 112 of the trocar 110 and the entirety of the housing 120, including the first port 121 and the second port 122. The line A-A indicates a cross-section in which the views of FIGS. 4-6 will be taken.

Figure 4:
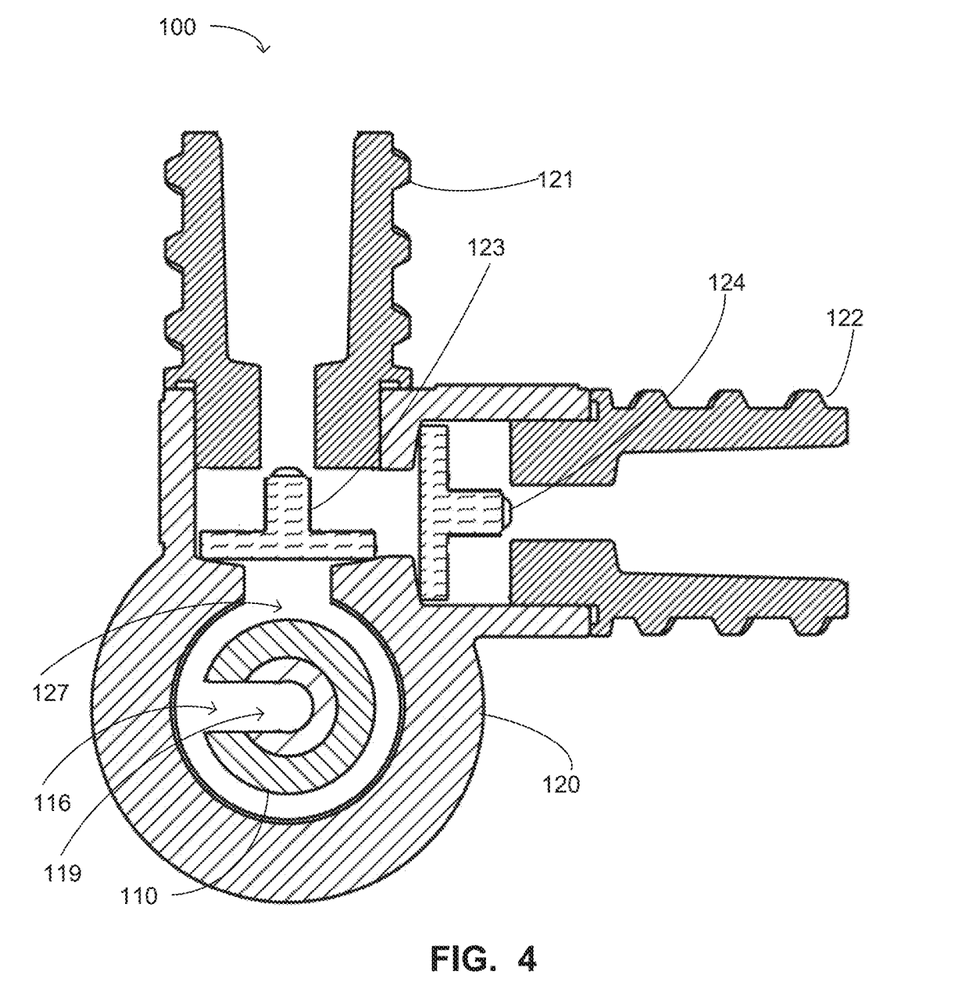
FIG. 4 provides a cross-sectional view, taken along the line A-A in FIG. 3, of a portion of the medical device of FIG. 1 in a zero-pressure configuration, in accordance with embodiments herein.

FIG. 4 provides a cross-sectional view, taken along the line A-A in FIG. 3, of a portion of the medical device 100 in a zero-pressure configuration, in accordance with embodiments herein. By "zero-pressure" is meant that either no syringe is attached to the first port 121 or the plunger of a syringe attached to the first port 121 is not being moved.

FIG. 4 shows the cannulation 119 of the trocar 110, as well as an exit fenestration 116. The cannulation 119 and the exit fenestration 116 of the trocar 110 are in fluid communication with the longitudinal cavity 127 of the housing 120. With zero pressure or substantially zero pressure being applied through the first port 121, the first valve 123 is closed, thereby preventing fluid flow out of the continuous space formed by the cannulation 119, the exit fenestration 116, and the longitudinal cavity 127. The zero-pressure configuration also maintains the second valve 124 in a closed position, thereby preventing fluid flow out the second port 122.

Figure 5:
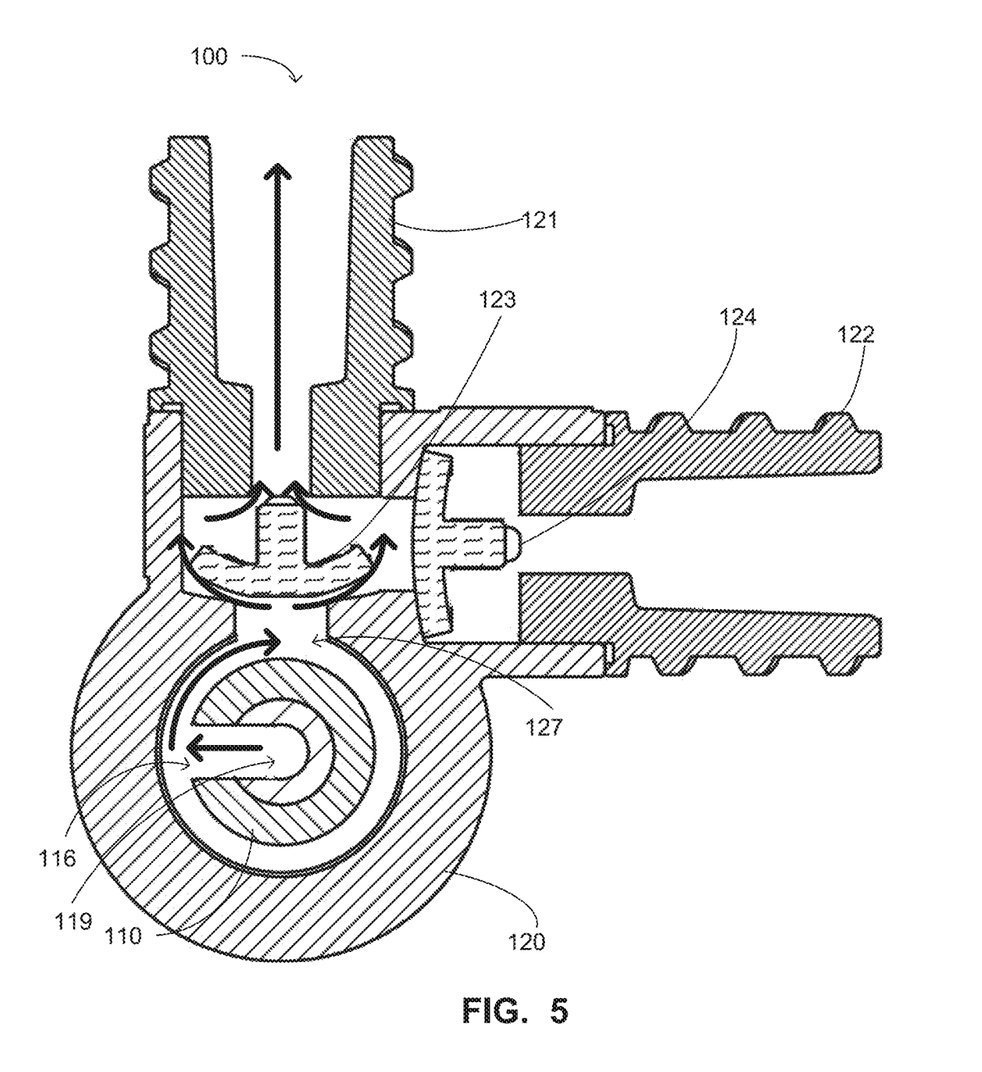
FIG. 5 provides a cross-sectional view, taken along the line A-A in FIG. 3, of a portion of the medical device of FIG. 1 in a negative-pressure configuration, in accordance with embodiments herein.

FIG. 5 provides a cross-sectional view, taken along the line A-A in FIG. 3, of the portion of the medical device 100 in a negative-pressure configuration, in accordance with embodiments herein. By "negative-pressure" is meant that the plunger of a syringe attached to the first port 121 is being withdrawn, i.e., a vacuum is being applied from the first port 121.

In the negative-pressure configuration, the first valve 123 is opened by vacuum deflection. As a result, fluid flows in the directions of the heavy arrows shown in FIG. 5. Put into words, fluid flows from the cannulation 119 of the trocar 110, out the exit fenestration 116 of the trocar 110, through the longitudinal cavity 127 of the housing 120, around the open first valve 123, and out the first port 121. When the medical device 100 is deployed with the first end 111 of the trocar 110 disposed in a bone marrow space of a bone, the negative-pressure configuration shown in FIG. 5 will draw bone marrow into a syringe attached to the first port 121 of the housing 120.

As will be apparent from FIG. 5, the second valve 124 remains closed in the negative-pressure configuration. Accordingly, substantially no fluid flows out the second port 122.

Figure 6:
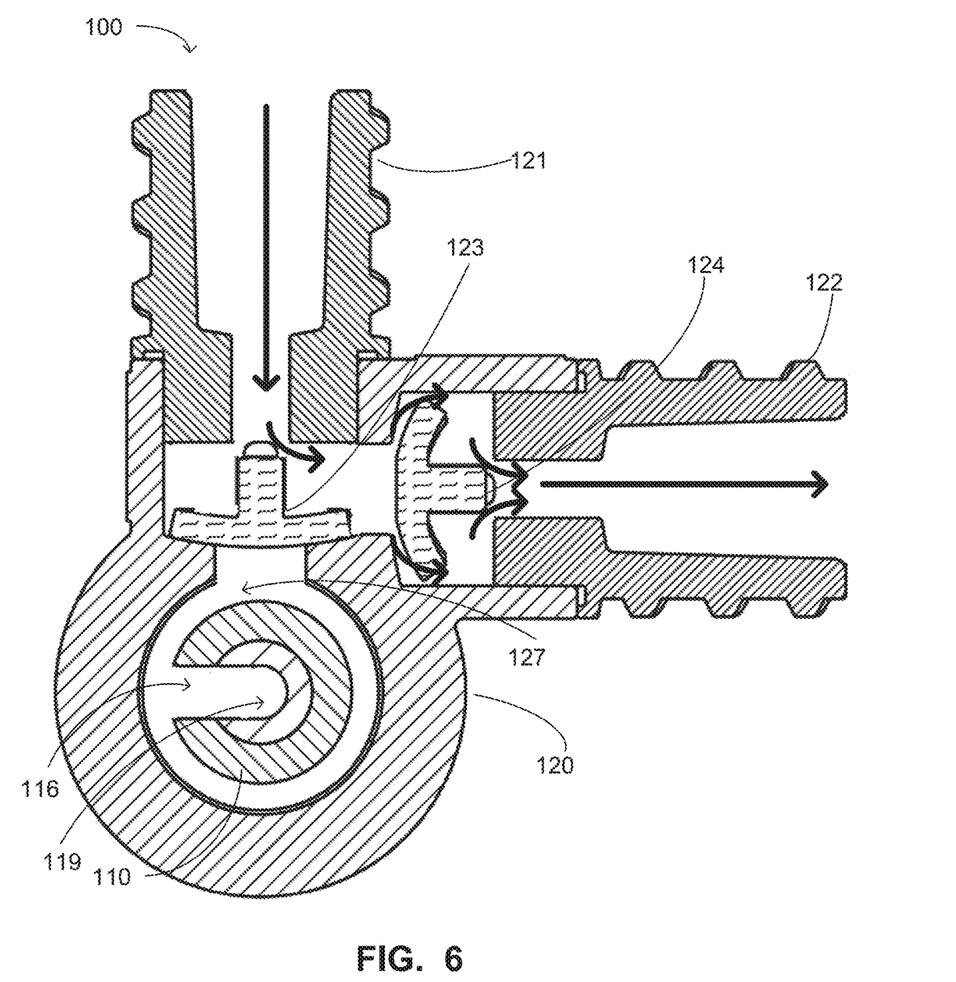
FIG. 6 provides a cross-sectional view, taken along the line A-A in FIG. 3, of a portion of the medical device of FIG. 1 in a positive-pressure configuration, in accordance with embodiments herein.

FIG. 6 provides a cross-sectional view, taken along the line A-A in FIG. 3, of the portion of the medical device 100 in a positive-pressure configuration, in accordance with embodiments herein. By "positive-pressure" is meant that the plunger of a syringe attached to the first port 121 is being pushed in, i.e., any fluid in the syringe is being injected into the housing 120 via the first port 121.

In the positive-pressure configuration, the first valve 123 is closed by fluid pressure and the same fluid pressure opens the second valve 124. As a result, fluid flows in the directions of the heavy arrows shown in FIG. 6. Put into words, fluid flows from the first port 121, around the open second valve 124, and out the second port 122. The closed first valve 123 prevents fluid flow into the longitudinal cavity 127, the exit fenestration 116, and the cannulation 119. When a syringe attached to the first port 121 contains bone marrow prior to application of positive pressure, bone marrow will be collected in a syringe or other collection vessel attached to the second port 122.

Figure 7:
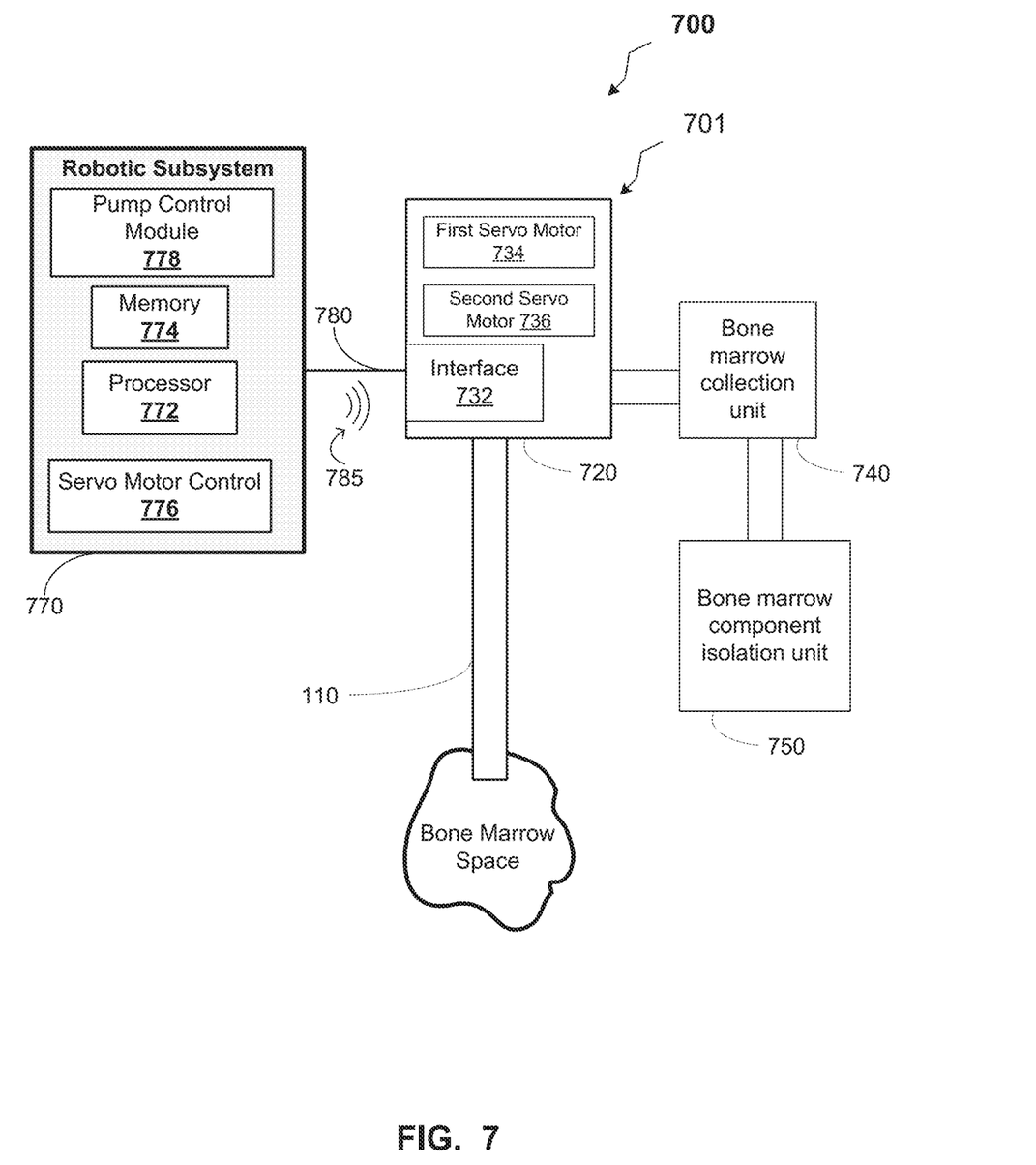
FIG. 7 schematically illustrates a medical device system comprising a medical device comprising a trocar and a housing, in accordance with embodiments herein.

FIG. 7 schematically illustrates a stylized depiction of a medical device system 700, in accordance with embodiments herein. The medical device system 700 comprises a medical device 701. The medical device 701 comprises a trocar 110, as described above, and a housing 720. In one embodiment, the housing 720 is substantially identical to the housing 120 described above, except for further comprising an interface 732 for the receipt of input signals from and/or the transmission of output signals to a robotic subsystem 770. The housing 720 also further comprises a first servo motor 734 for opening and closing the first valve 123 and the second valve 124, e.g., by applying zero, negative, or positive pressure to diaphragms as depicted in FIGS. 2 and 4-6, based on particular input signals from the robotic subsystem 770. The housing 720 additionally further comprises a second servo motor 736 for rotating the trocar 110, e.g., by rotating the handle 114 of the trocar 110 depicted in FIGS. 1-2.

The robotic subsystem 770 may be capable of automatically performing one or more tasks described herein. The robotic subsystem 770 may comprise a pump control module 778 that provides for control of a pump within the apparatus 100. The pump control module 778 may communicate with the pump of the medical device 701 by wired communication circuit 780 and/or wireless communication circuit 785 (e.g., Bluetooth™, 802.11x, cellular, etc., communication circuits).

The robotic subsystem 770 may comprise a memory unit 774 that is capable of storing various types of data, including program/software data, system control data, results data, etc. The robotic subsystem 770 may also comprise a processor 772. The processor 772 may be a micro-processor, a microcontroller, a field programmable gate array (FPGA), an application-specific integrated circuit (ASIC), or the like. The processor is capable of controlling the operations of the robotic subsystem 770.

The robotic subsystem 770 may also control a servo motor controller 776. The servo motor controller 776 is capable of controlling one or more servo type motors 734, 736 that control the operations of various components of the system 700, such as the position of the medical device 701 relative to a patient's body, the insertion or withdrawal of the trocar 110 from a bone marrow space of the patient's body, the application of zero, negative, or positive pressure by a syringe attached to a first port 121 of the housing 720, etc. The servo motor controller 776 may be programmed and/or controlled by the processor 772.

One or more of the components of the robotic subsystem 770 may be a hardware device, a software module, a firmware module, and/or a combination thereof. In some embodiments, the various method steps described above may be fully automated and controlled by the robotic subsystem 770.

Bone marrow expelled from the housing 720 during the positive-pressure configuration may be collected by a bone marrow collection unit 740. The bone marrow collection unit 740 may comprise a syringe.

In embodiments, such as the embodiment depicted in FIG. 7, the medical device system 700 may further comprise a bone marrow component isolation unit 750. The bone marrow component isolation unit 750 may comprise one or more subunits configured to process bone marrow collected in bone marrow collection unit 740 in order to isolate one or more desired components of the bone marrow. In one embodiment, the bone marrow component isolation unit 750 is configured to isolate mesenchymal stem cells from collected bone marrow.

Figure 8:
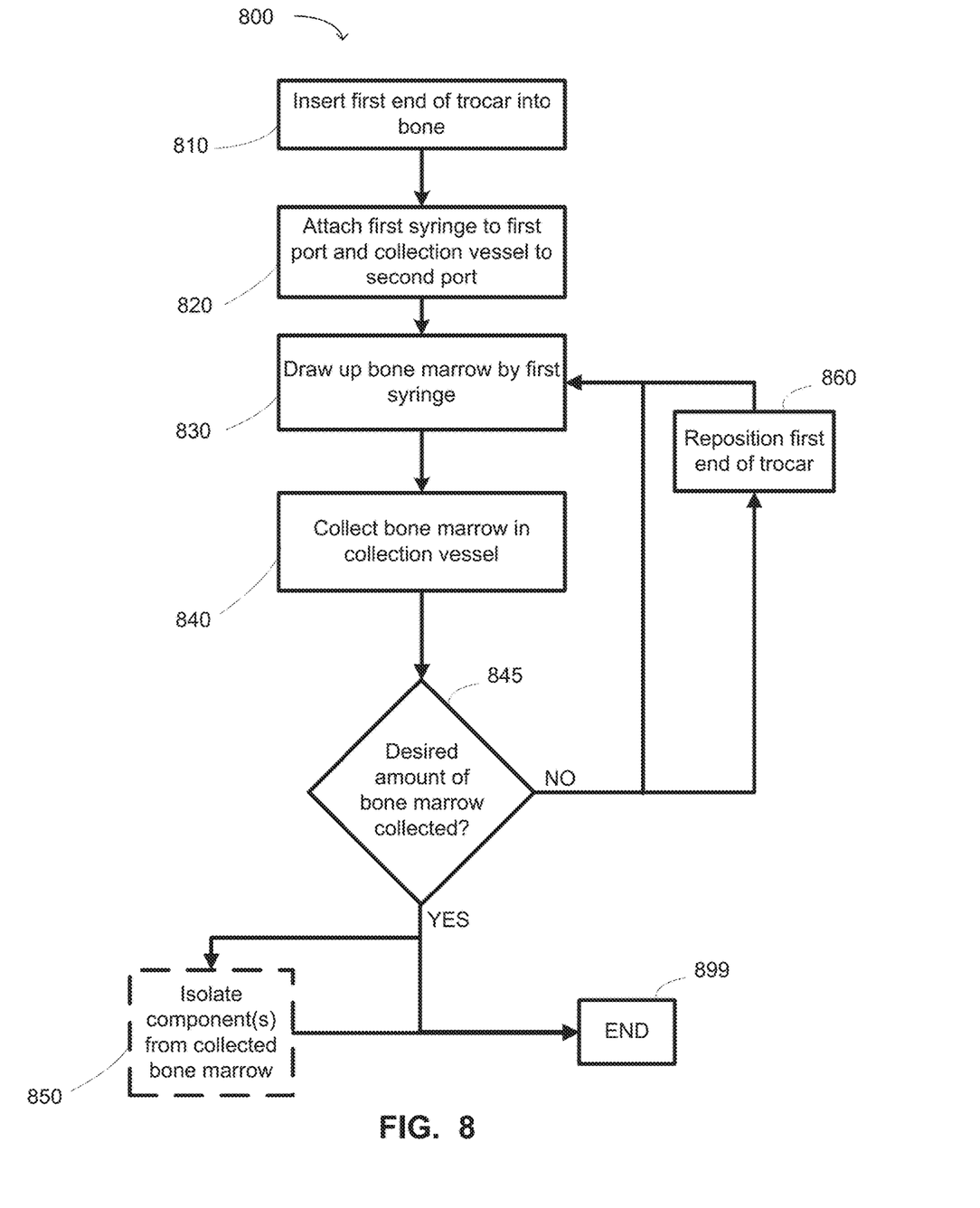
FIG. 8 provides a flowchart depicting a method of collecting bone marrow from bone, in accordance with embodiments herein.

FIG. 8 provides a flowchart depicting a method 800 of collecting bone marrow from bone, in accordance with embodiments herein. The method 800 comprises inserting (at 810) a first end of a trocar into a bone, wherein the trocar is a component of a medical device comprising the trocar, wherein the trocar comprises a cannulation and at least one fenestration proximal the first end, and a housing comprising a first port configured for the attachment of a first syringe and a second port configured for the attachment of a collection vessel, a first valve configured to selectively permit fluid flow from the at least one fenestration of the trocar through the cannulation of the trocar to the first port, and a second valve configured to selectively permit fluid flow from the first port to the second port.

In one embodiment, the first valve and the second valve are diaphragms configured to be deformable upon the application of positive or negative pressure. Alternatively or in addition, in one embodiment, the trocar comprises two fenestrations.

In one embodiment, the first end is rigid and pointed, and inserting (at 810) comprises hammering or pushing the first end into the bone. Alternatively or in addition, in one embodiment, the first end is rigid, pointed, and threaded, and inserting (at 810) comprises drilling or screwing the first end into the bone.

In one embodiment, the bone is located within the living body of a mammal. In a particular embodiment, the mammal is a human being.

The method 800 also comprises attaching (at 820) a first syringe to the first port and a collection vessel to the second port. The method 800 additionally comprises drawing up (at 830) bone marrow from the bone by the first syringe, and collecting (at 840) the bone marrow in the collection vessel.

In one embodiment, drawing up (at 830) the bone marrow comprises applying negative pressure to the first valve by the first syringe.

In one embodiment, collecting (at 840) the bone marrow comprises applying positive pressure to the first valve and the second valve by the first syringe.

After collecting (at 840) the bone marrow, a determination may be made (at 845) as to whether a desired amount of bone marrow has been collected. If a desired amount of bone marrow has not been collected, flow returns to drawing up (at 830) bone marrow by the first syringe. Prior to drawing up (at 830), the first end of the trocar may be repositioned (at 860). Repositioning (at 860) may comprise rotating the trocar, which may bring the at least one fenestration into contact with unharvested bone marrow, may provide a force disrupting the gross structure of the bone marrow to allow easier harvesting of bone marrow, or both; and/or longitudinally translating the trocar, i.e., moving the first end of the trocar further into a further out of the bone marrow space, which may bring the at least one fenestration into contact with unharvested bone marrow, may provide a force disrupting the gross structure of the bone marrow to allow easier harvesting of bone marrow, or both.

If the determination (at 845) is that a desired amount of bone marrow has been collected, flow may pass to isolating (at 850) at least one component from the collected bone marrow. In one embodiment, isolating (at 850) may comprise isolating mesenchymal stem cells from the collected bone marrow. Whether or not flow passes to isolating (at 850), flow terminates at end 899.

The particular embodiments disclosed above are illustrative only, as the disclosure may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is, therefore, evident that the particular embodiments disclosed above may be altered or modified and all such variations are considered within the scope and spirit of the disclosure. Accordingly, the protection sought herein is as set forth in the claims below.

What is claimed is:

1. A medical device, comprising:
 a trocar having a first end and a second end, and comprising:
  a cannulation and a first fenestration proximal the first end, a second fenestration proximal the second end, and a handle proximal the second end;
  a first groove formed into an outer surface of the trocar and between the first and second ends;
  a second groove formed into the outer surface of the trocar and between the first and second ends; and
  a first rotation permitting seal positioned in the first groove and between the trocar and the housing;
  a second rotation permitting seal positioned in the second groove and between the trocar and the housing; and
 a housing comprising a first port configured for the attachment of a first syringe and a second port configured for the attachment of a collection vessel, a longitudinal cavity surrounding the second fenestration of the trocar and forming an annulus therearound, a first valve configured to selectively permit fluid flow from the longitudinal cavity through the first port, and a second valve configured to selectively permit fluid flow from the first syringe through the second port.

2. The medical device of claim 1, wherein the first valve and the second valve are diaphragms configured to be deformable upon the application of positive or negative pressure.

3. The medical device of claim 1, wherein the first end is rigid and pointed.

4. The medical device of claim 3, wherein the first end is rigid, pointed, and threaded.

5. The medical device of claim 1, further comprising:
 a first syringe attached to the first port of the trocar; and a collection vessel attached to the second port of the trocar.

6. The medical device of claim 1, wherein the first port and the second port each comprise a luer fitting.

7. A method, comprising:
inserting a first end of a trocar into a bone, wherein the trocar is a component of a medical device comprising:
the trocar, wherein the trocar comprises:
a cannulation and a first fenestration proximal the first end, a second fenestration proximal a second end, a handle proximal a second end;
a groove formed into an outer surface of the trocar and between the first and second ends;
a rotation-permitting seal configured to maintain a longitudinal position of the trocar relative to the housing while permitting rotation of the trocar relative to the housing;
a housing comprising a first port configured for the attachment of a first syringe and a second port configured for the attachment of a collection vessel, a longitudinal cavity surrounding the second fenestration of the trocar and forming an annulus therearound, a first valve configured to selectively permit fluid flow from the longitudinal cavity through the first port, and a second valve configured to selectively permit fluid flow from the through the second port; and
attaching a first syringe to the first port and a collection vessel to the second port;
drawing up bone marrow from the bone by the first syringe;
collecting the bone marrow in the collection vessel;
rotating the trocar relative to the housing; and
repeating the drawing up of the bone marrow and the collecting of the bone marrow.

8. The method of claim 7, wherein the first end is rigid and pointed, and inserting comprises hammering or pushing the first end into the bone.

9. The method of claim 7, wherein the first end is rigid, pointed, and threaded, and inserting comprises drilling or screwing the first end into the bone.

10. The method of claim 7, wherein the bone is located within the living body of a mammal.

11. The method of claim 10, wherein the mammal is a human being.

12. The method of claim 7, wherein the first valve and the second valve are diaphragms configured to be deformable upon the application of positive or negative pressure.

13. The method of claim 12, wherein drawing up the bone marrow comprises applying negative pressure to the first valve by the first syringe.

14. The method of claim 12, wherein collecting the bone marrow comprises applying positive pressure to the first valve and the second valve by the first syringe.

15. The method of claim 7, further comprising isolating at least one component from the collected bone marrow.

16. A medical device system, comprising:
a medical device, comprising:
a trocar having a first and a second end and comprising:
a cannulation, a first fenestration proximal the first end and a second fenestration proximal the second end;
a groove formed into an outer surface of the trocar and between the first and second ends;
a rotation-permitting seal configured to maintain a longitudinal position of the trocar relative to the housing while permitting rotation of the trocar relative to the housing;
a housing comprising a first port configured for the attachment of a first syringe and a second port configured for the attachment of a collection vessel, a longitudinal cavity surrounding the second fenestration of the trocar and forming an annulus therearound, a first valve configured to selectively permit fluid flow from the longitudinal cavity through the first port, and a second valve configured to selectively permit fluid flow from the first syringe through the second port;
a first servo motor configured to open and close the first valve and the second valve;
a second servo motor configured to rotate the trocar; and
a robotic subsystem, comprising:
at least one servo motor controller configured to control the first servo motor and the second servo motor; and
a controller configured to control the operation of the robotic subsystem.

17. The medical device system of claim 16, further comprising a bone marrow component isolation unit.

* * * * *